(12) United States Patent
Schultheis et al.

(10) Patent No.: US 11,408,606 B2
(45) Date of Patent: Aug. 9, 2022

(54) ILLUMINATION SYSTEM WITH A LIGHT GUIDE AND AN EMISSION ELEMENT

(71) Applicant: SCHOTT AG, Mainz (DE)

(72) Inventors: Bernd Schultheis, Schwabenheim (DE); Oliver Keiper, Hünstetten (DE); Hubertus Russert, Jugenheim (DE); Andreas Dietrich, Guldental (DE)

(73) Assignee: SCHOTT AG, Mainz (DE)

(*) Notice: Subject to any disclaimer, the term of this patent is extended or adjusted under 35 U.S.C. 154(b) by 0 days.

(21) Appl. No.: 17/010,111

(22) Filed: Sep. 2, 2020

(65) Prior Publication Data

US 2021/0063011 A1    Mar. 4, 2021

(30) Foreign Application Priority Data

Sep. 2, 2019    (DE) ..................... 10 2019 123 448.4

(51) Int. Cl.
*F21V 7/04*        (2006.01)
*F21V 33/00*    (2006.01)
(Continued)

(52) U.S. Cl.
CPC .......... *F21V 33/0068* (2013.01); *A61N 5/062* (2013.01); *F21K 9/61* (2016.08);
(Continued)

(58) Field of Classification Search
CPC ........ F21K 9/61; F21V 21/32; F21V 33/0068; A61N 2005/063; A61N 5/062;
(Continued)

(56) References Cited

U.S. PATENT DOCUMENTS 5,011,247 A * 4/1991 Boudreau ............ G02B 6/4208
385/33
5,290,275 A 3/1994 Kittrell
(Continued)

FOREIGN PATENT DOCUMENTS

CA        1096214           2/1981
CN    201323378 Y  * 10/2009
(Continued)

OTHER PUBLICATIONS

USP Class VI, "1031 The Biocompatibility of Materials Used in Drug Containers, Medical Devices, and Implants", 7 pages.
(Continued)

*Primary Examiner* — Omar Rojas Cadima
(74) *Attorney, Agent, or Firm* — Ruggiero McAllister & McMahon LLC

(57) ABSTRACT

An illumination system is provided that includes a laser light source, a light guide, a connector, and an emission element. The laser light source has a numerical aperture. The light guide has a proximal end and a distal end. The connector has a connector housing and connects and/or assigns the laser light source at the proximal end. The emission element is at the distal end. The connector housing has a device that reduce an influence of a range of variation of the numerical aperture so that an emission behaviour of the emission element is independent of a range of variation of the numerical aperture.

19 Claims, 4 Drawing Sheets

(51) Int. Cl.
*F21K 9/61* (2016.01)
*F21K 9/65* (2016.01)
*F21K 9/69* (2016.01)
*A61N 5/06* (2006.01)
*F21V 21/32* (2006.01)
*G02B 6/42* (2006.01)
*G02B 6/26* (2006.01)
*F21W 131/20* (2006.01)
*A61N 5/067* (2006.01)

(52) U.S. Cl.
CPC .................. *F21K 9/65* (2016.08); *F21K 9/69* (2016.08); *F21V 21/32* (2013.01); *G02B 6/262* (2013.01); *G02B 6/4204* (2013.01); *A61N 5/067* (2021.08); *A61N 2005/063* (2013.01); *F21W 2131/20* (2013.01)

(58) Field of Classification Search
CPC .... A61N 2005/0602; A61B 2018/2205; A61B 18/22; A61B 2018/00404; G02B 27/0994; G02B 19/0028; G02B 6/4202; G02B 6/4204; G02B 6/0008; G02B 6/0006; G02B 6/0096; G02B 6/02395; G02B 19/0052; F21S 41/24; F21S 41/16; F21S 41/176
See application file for complete search history.

(56) References Cited

U.S. PATENT DOCUMENTS

| | | | |
|---|---|---|---|
| 5,311,614 A | | 5/1994 | Caron |
| 5,754,716 A | | 5/1998 | Kim |
| 6,480,659 B1 * | | 11/2002 | Patlakh .............. G02B 6/02228 372/6 |
| 9,304,271 B2 | | 4/2016 | Dietrich |
| 2004/0233388 A1 | | 11/2004 | Artsyukhovich |
| 2006/0098934 A1 | | 5/2006 | Eyal |
| 2006/0152926 A1 | | 7/2006 | Hama |
| 2008/0279523 A1 * | | 11/2008 | Fujimoto ........... G02B 27/0994 385/137 |
| 2015/0085516 A1 | | 3/2015 | Brune |
| 2018/0113246 A1 | | 4/2018 | Rose |
| 2019/0243074 A1 | | 8/2019 | Mach |
| 2020/0222712 A1 | | 7/2020 | Schultheis |

FOREIGN PATENT DOCUMENTS

| | | | |
|---|---|---|---|
| DE | 2748503 | 8/1978 | |
| DE | 4026452 | 3/1992 | |
| DE | 102007028081 | 11/2008 | |
| DE | 102007027081 | 12/2008 | |
| DE | 102017122756 | 4/2019 | |
| DE | 102018133338 | 6/2020 | |
| EP | 0021473 A1 * | 1/1981 | .......... G02B 6/4204 |
| EP | 0898186 | 2/1999 | |
| EP | 2407807 | 1/2012 | |
| WO | WO-2005073771 A1 * | 8/2005 | ............ G01J 3/4406 |

OTHER PUBLICATIONS

ISO 11135, "Sterilization of health-care products—Ethylene oxide—Requirements for the development, validation and routine control of a sterilization process for medical devices", Second Edition, Jul. 15, 2014, 88 pages.
ISO 10993-1, "Biological evaluation of medical devices—Part 1: Evaluation and testing within a risk management process", Fifth Edition, Aug. 2018, 48 pages.
DIN EN ISO 10993-5, "Biological evaluation of medical devices—Part 5: Tests for in vitro cytotoxicity (ISO 10993-5:2009) English version of DIN EN ISO 10993-5:2009-10", Oct. 2009, 44 pages.
Hasan, "Photodynamic Therapy of Cancer", Cancer Medicine 2003.
"Laser-induced interstitial thermotherapy (LITT) for malignant tumors" HTA report by the German Medical Association and the National Association of Statutory Health Insurance Physicians, May 24, 2002.

* cited by examiner

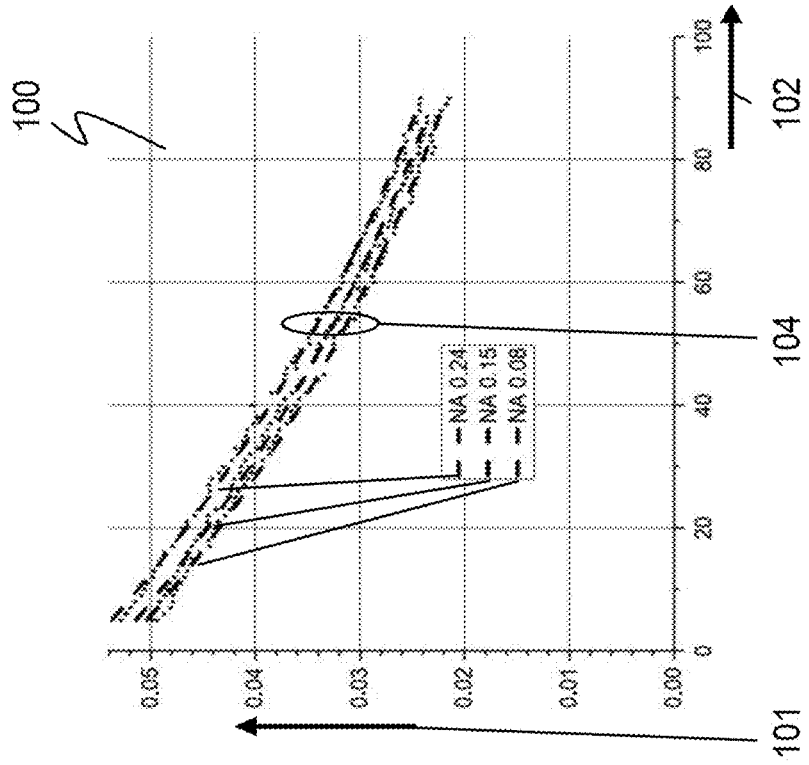
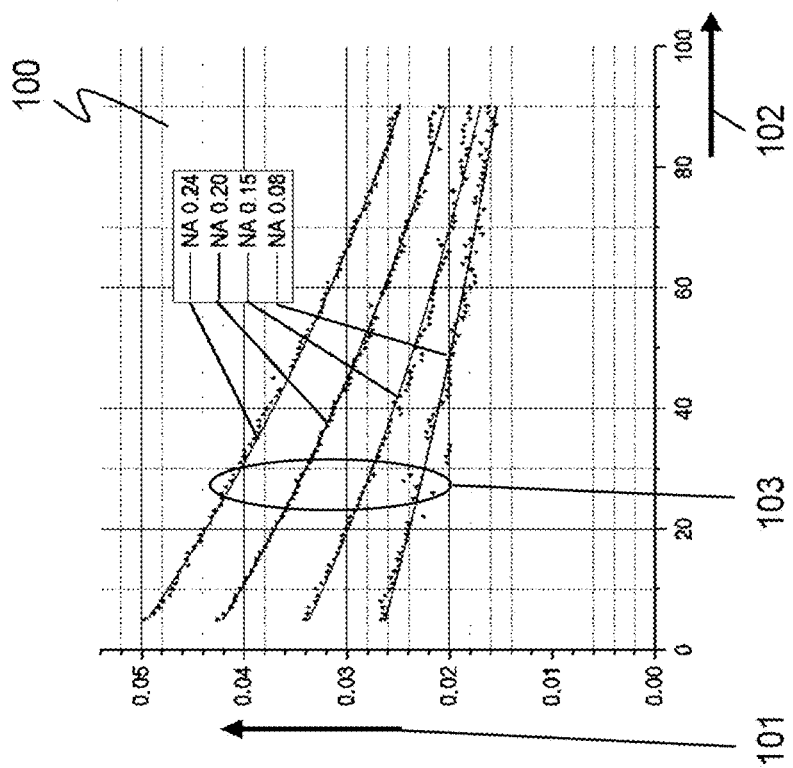
Fig. 5b
Fig. 5a

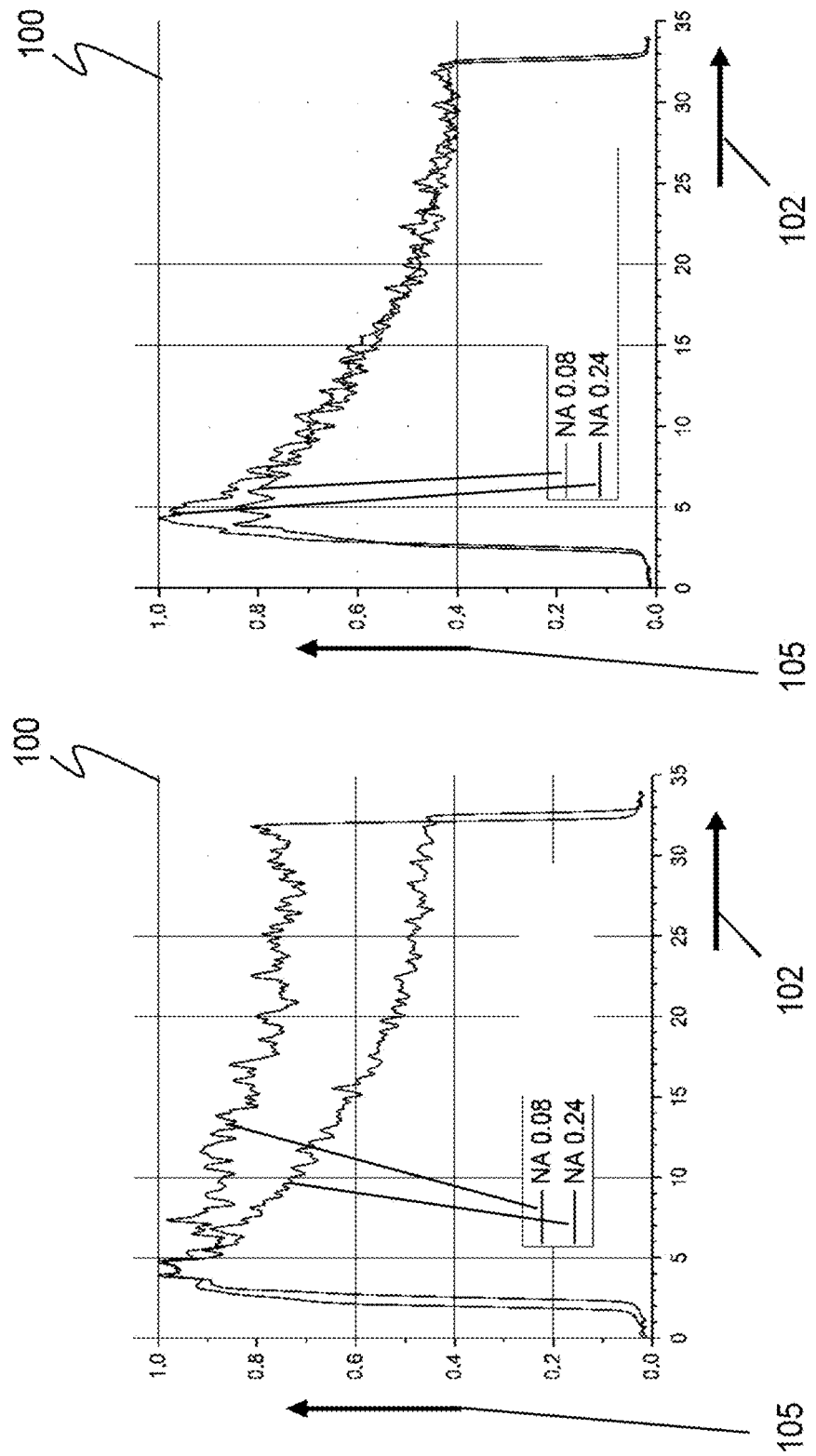

ILLUMINATION SYSTEM WITH A LIGHT GUIDE AND AN EMISSION ELEMENT

CROSS REFERENCE TO RELATED APPLICATIONS

This application claims benefit under 35 USC § 119 of German Application No. 10 2019 123 448.4 filed Sep. 2, 2019, the entire contents of which are incorporated herein by reference.

BACKGROUND

1. Field of the Invention

The invention relates to an illumination system comprising at least one laser light source with a numerical aperture $NA_L$ and a light guide which is connectable and/or assignable at a proximal end to the at least one laser light source by means of a connector with a connector housing and having an emission element at the distal end of the light guide.

2. Description of Related Art

Illumination systems find increasing use in medicine. Currently, it is possible to classify the following focuses of application: photodynamic therapy (PDT) or photoimmunotherapy (PIT) for tumour therapy, endovenous laser treatment (EVLT) for treating varicose veins, laser interstitial thermal therapy (LITT), and other applications, inter alia in the fields of dentistry, ophthalmology or dermatology.

Photodynamic therapy (PDT) is a minimally invasive option for therapy in the case of various cancers. PVD is understood to be a method for treatment of tumours and other tissue changes (such as neovascularization) using light in combination with a light activatable substance. At the start of the treatment, light-sensitive substances, so-called photosensitizers, are injected into the patient's bloodstream intravenously, said substances accumulating in or on the cancerous cells. These natural photo substances accumulate in the tumour cells and cause a pronounced light sensitivity there. To this end, a plurality of cannulas (typically up to 8) are pierced into the tumour tissue and a light guide with a diffuser element is introduced into each cannula, the diffuser elements having to be disposed in spatially distributed fashion over the tumour tissue. Laser light, as a rule with wavelengths in the visible spectral range, for example green light with a wavelength of 532 nm or red light with a wavelength of 690 nm, is coupled into the diffuser elements by the light guides such that the tumour tissue is illuminated as uniformly as possible from the inside. In the process, aggressive oxygen radicals form in these cells and selectively destroy the tumour cells. In contrast to the diseased cells, the healthy cells remain untouched by this chemical reaction. The precise mode of action is described, inter alia, in "Photodynamic Therapy of Cancer", Cancer Medicine 2003.

Photoimmunotherapy (PIT) represents a similar method, in which an immune reaction is triggered in the presence of a photoactivatable medicament and the cancerous cells necrotize as a result.

Here, a distinction is made between cylindrical diffusers with typical active lengths of 10 to 50 mm, spot diffusers or else frontal diffusers, which generate a forwardly directed illumination cone, and point emitters or spherical emitters or diffusers which have a radial light emission.

What it comes down to in the operating state of cylindrical diffusers is that, in particular, a lateral emission of the diffuser elements should be as homogeneous as possible over their length. This applies both axially, i.e., the emission intensity is the same within the scope of the homogeneity requirements at all points along any line from the proximal to the distal end in the direction of the longitudinal axis, and radially, i.e., the emission intensity is also same within the scope of the homogeneity requirements at all points on any circumferential line along the longitudinal axis, as a result of which these diffusers almost act as Lambertian emitters.

In the case of the aforementioned diffusers, it may be desirable that the emission is not implemented with the same intensity in all possible spatial directions of the respective diffuser. In an advantageous embodiment, the diffusers can be provided with apparatuses, at least in portions or in sections, for example in a grid-like or gradient-like fashion, in accordance with the required emission characteristic, said apparatuses being transparent, having a reduced transmission, and/or being translucent and/or being opaque in order to at least reduce and/or else completely suppress the transmission of emitted radiation. These can be designed over a wavelength range or else in wavelength-selective fashion, and consequently can be designed as a filter. It is likewise conceivable for these to facilitate specular or diffuse reflection into the respective diffuser or back again; they could be configured, for example, as coatings, lacquers or printing or as comprising a combination thereof. Here, a coating could also comprise metallic and/or dielectric layers.

At the same time, high scattering efficiency must also be obtained in order to ensure as little heat flux into the tissue as possible. Typical homogeneity requirements in respect of the lateral emission lie at no more than ±10 to 20% deviation from the mean intensity, wherein a forwardly directed emission, in particular out of the distal end, of more than 10% of the input coupled light, typically no more than 5%, should be avoided. The typical laser power is <5 W continuous power in the case of PDT applications, and so no more than between 100 mW and 1000 mW, typically between 200 mW and 500 mW, are emitted per cm diffuser length. This currently allows the use of plastic-based diffuser approaches.

In the case of EVLT, the treating physician introduces a catheter into the affected vein via a tiny puncture site, said catheter serving as a guide for the vein laser. As a result of the targeted lateral emission of the laser power by means of the diffuser, the vessel inner wall is subsequently strongly heated, leading to the vein collapsing and becoming sealed. The pathological return flow of the venous blood is consequently prevented. As a consequence, the vein hardens, regresses and is able to be broken down by the body. As a rule, so-called ring or double ring fire systems are currently used as emission elements in this case. The laser light is emitted radially in the form of a relatively sharply delimited ring or double ring light to the tissue surrounding the vein. Here, for uniform treatment, the light guide with the emission element is often manually pulled through the vein section to be treated at a rate that is as constant as possible; this complicates the application, since further cell damage may arise at a site in the case of non-compliance or excessive dwell time.

A cylindrical diffuser of the kind used in PDT applications would bring advantages here. However, EVLT treatment requires significantly higher laser powers. By way of example, laser power is typically between 10 and 50 W at wavelengths in the NIR range, i.e., between approximately 800 nm and 1480 nm, which is currently provided using diode lasers (for example, 810 nm, 940 nm, or 1480 nm) or Nd:YAG lasers (1064 nm). In the meantime, longer wavelengths around 2 μm have also become established for EVLT treatment. In this case, Tm:YAG lasers (1.9 μm) and Ho:YAG lasers (2.1 μm) are used, for example. On account of the absorption properties of tissue, lower laser powers, typically <10 W, are required at these wavelengths. However, the use of light guides made of fused silica is already mandatory here, in particular for supplying the laser light.

The homogeneity requirements on lateral emission of diffusers which can be employed for EVLT are less high compared to those of a PDT application and can amount to a maximum deviation of at most ±30% to at most ±50% from the average intensity.

LITT is a minimally invasive method that is used for local tumour destruction. The tumour is punctured under visualization (e.g., sonography/MRI), one (or more) laser fibre(s) are introduced into the focus of the tumour, and sclerosis is induced in the latter by thermal energy. In particular Nd:YAG lasers (1064 nm) and diffuser tip applicators are used in this case. The laser power is approximately 5 to 8 W (e.g., in "Laserinduzierte Interstitielle Thermotherapie (LITT) bei malignen Tumoren" BÄK and KBV, 2002).

DE 102017122756 A1 describes a corresponding embodiment for a cylindrical diffuser, which has a substantially radial, homogeneous emission characteristic.

DE 102018133338 by the applicant, currently unpublished, describes an embodiment of a spherical diffuser with a largely spherical emission characteristic.

However, what was found in all these approaches is that both the uniformity and the efficiency of the emission of the diffuser depends significantly on the numerical aperture, that is to say on the emission characteristic of the radiation of the light source, in particular a laser light source, i.e., on the numerical aperture of the laser $NA_L$, of the coupling or radiation into the light guide and the transfer of the guided radiation into the diffuser, for example in a quartz fibre. Comparatively large fluctuations or changes or variations in the laser $NA_L$, caused in part by the use of different laser types (style of the laser or even the same laser style but from different manufacturers) and/or else caused by manufacturing variations in the case of the lasers or laser modules and/or by misalignment and/or by thermal effects during practical use, lead to a significant range of variation in the emission characteristic and in the efficiency of the diffuser. Expressed differently, a demanded or specified homogeneity of the emission intensity of an emission element, for example in units of relative luminance or the deviation thereof from a mean or maximum value, is not obtained in the case of changes in the numerical aperture of the laser $NA_L$ or cannot be obtained or cannot be maintained in a system made of laser, light guide and emission element, initially adjusted per se, in the case of changes in the laser light source, in particular in the $NA_L$ thereof.

So-called mode mixers can help reduce the range of variation in this case.

In principle, a use of, e.g., quartz fibres with a non-round core region, for example so-called hex fibres with a 6-sided hexagonal fibre core, can be used as a mode mixer. However, these are comparatively expensive to produce as they require specific preforms.

The literature has also disclosed purely mechanical methods for mode mixing, in which the fibre is bent in targeted fashion. Thus, DE 102007028081 B3, for example, describes a laser device for generating laser beams with a certain beam profile, comprising a laser and a light guide coupled to the laser. Therein, provision is made for at least two first abutment elements for the optical waveguide to be arranged at a distance from one another on the one side of the optical waveguide, for a second abutment element to be situated on the opposite side of the optical waveguide between the two first abutment elements and for at least one of the abutment elements to be coupled to an actuation mechanism and for the actuation mechanism to have a drive for an actuating element, wherein the actuating element is connected to a path measuring device with an electrical measurement signal output and the drive for the actuating element, the path measuring device and a control device are connected to one another, in such a way that a mixed mode, a ring mode and a ring mode with a core are continuously generable in succession by way of a curvature of the optical waveguide that is determined by the position of the abutment elements. This document describes the fundamental principle of mechanically-based mode mixing, including an apparatus with which mode mixing is adjustable in targeted fashion. However, no specific approaches as to how this can be realized in cost-effective and practical fashion for the applications set forth at the outset are disclosed.

EP 2407807 A2 describes a light fibre arrangement for transporting a laser beam, which is used for material processing and present at the output of an output fibre in a fundamental mode beam quality, comprising a multi-mode mixing fibre which has a curved profile over at least part of its length for mixing the modes propagating therein and which has a larger numerical NA than the NA of the output fibre which provides the laser beam at the input of the multimode mixing fibre and which is coupled to the input of the multimode mixing fibre, and in which a multimode transport fibre is provided for transporting the laser beam available at the output of the multimode mixing fibre to a process location, the NA of which is greater than or equal to the numerical aperture of the multimode mixing fibre. Such an approach may be expedient for the laser processing machines but cannot be used, for example, for medical therapy, in particular for such a medical therapy in which the light guide or component comprising a light guide is used as a so-called disposable, i.e., as a single-use and preferably miniaturized light guiding system with corresponding emission elements.

A further approach in the prior art is that, for example, a quartz fibre serving as a light guide is exposed locally to a punctiform mechanical load by means of 3 small balls in a special sleeve. Here, these balls press into the usually thermoplastic buffer material of the quartz fibre. A disadvantage here is that, depending on the ambient temperature or the temperature of use, the mechanical pressure on the fibre generated thus is not defined on account of a certain plastic deformation of the buffer material and may change over time and/or that uncontrolled, local loads or radii of curvature that are too small, which at least damage the fibre, set in. Moreover, such an approach represents additional outlay in manufacturing.

US 2018/0113246 A1 describes various approaches for cylindrical and frontal diffusers for photoimmunotherapy (PIT), in which reference is likewise made, inter alia, to mode mixers and schematically describes, in FIG. 2 and FIG. 39 *a* to *d*, various approaches in which the quartz fibre used as a light guide is laid in loops and the like. However, no specific approaches are described therein as to how this can be implemented in respect of, firstly, a certain degree of robustness and, secondly, practicality.

SUMMARY

It is therefore an object of the invention to provide a cost-efficient solution, in particular a miniaturizable solution suitable for single use, for such mode mixers, which do not have the aforementioned disadvantages and, in particular, exert defined mechanical load on the light guide, and wherein an emission behaviour of the emission elements, as set forth at the outset, is substantially independent of a variation in the numerical aperture of a laser light source.

The object of the invention is achieved by virtue of the fact that the connector housing has devices for reducing an influence of a range of variation of the numerical aperture $NA_L$ of the laser light source of the laser light from the laser light source coupled into the connector, in such a way that the emission behaviour of the emission element is substantially independent of the range of variation of the numerical aperture $NA_L$. This facilitates a very cost-effective way of reducing the influence of an $NA_L$ variation or a change on the emission characteristic of, e.g., such components (emission elements), as described at the outset, to the effect that a range of variation of the input coupling NA of the laser light source $NA_L$ or of an input coupling fibre exerts virtually no more influence on, e.g., the homogeneity of the emission or else its efficiency. Particularly in the case of cylindrical diffusers, where it comes down to an intensity profile over the diffuser length that is as uniform as possible, this inventive measure can significantly stabilize the latter in respect of possible NA variations during input coupling. If the various NA values in the system of laser, light guide and diffuser are not matched to one another, it is not possible to achieve demanded, specified emission characteristics and/or emission intensities, or the spatial distribution thereof, of a diffuser. Particularly in the case where the $NA_L$ of the radiation of the employed laser changes, be it on account of changes of a laser per se, for example due to ageing, misalignment, the influence of temperature, etc., or on account of an exchange, replacement or use of an alternative laser, this influence on the emission characteristic or efficiency of an emission element can be significantly reduced by the approach according to the invention, virtually without any additional outlay. Here, the assumption can further be made that, as a rule, the NA values of the light guide (supply fibre) and of the diffuser (emission element) remain substantially constant or are substantially constant and these are designed to match one another. The latter holds true particularly in view of the fact that, in the case of cost-sensitive applications, it cannot be justifiable and by no means be practical to offer or keep available very different combinations of supply fibres and diffusers in order to react to the ageing of a laser, for example, or to compensate product variations in the case of the same laser modules per se. Accordingly, the connector housing comprises at least an apparatus, or is an apparatus, to at least reduce the influence of a changing or changeable numerical aperture of a laser on the emission, for example within the meaning of the emission intensity and emission homogeneity of an emission element.

Here, the connector housing in a receiving section for the light guide, has at least one guide element for bending at least one location of the light guide at least in part or in sections. What this bending can achieve is that various modes of light propagation mix in the light guide, and so it is possible to obtain an emission characteristic of the emission element that is largely stable in respect of NA variations of the light source.

Such a guide element, or else a plurality of guide elements such that a plurality of bends of the light guide can be achieved in part or in sections, can be configured, for example, as cylindrical and/or spherical, round studs and/or as studs with an oval or off-centred cross section or geometry and/or as spheres in order to guide the light guide, at least in the receiving section, in spatially defined fashion in respect of its relative position and, in the process, not drop below a certain minimum bend radius, which arises from the geometry and setup of the light guide.

In other words, the at least one guide element is configured, for example, as a cylindrical and/or conical stud and/or as a sphere, in order to guide the light guide, at least in the receiving section, in a defined spatial fashion in respect of its relative position and in order to maintain at least a minimum bend radius in the process.

With the specific embodiment thereof, the arrangement thereof and/or the number and/or uniform or combined geometric embodiment thereof, the guide elements can be used to define the at least one bend in the light guide.

In a specific embodiment variant, the connector housing can consist of at least two receiving shells disposed in the interior of the connector housing, wherein at least one of the receiving shells of the housing has the receiving section for receiving the light guide. According to the invention, the light guide has a profile that is bent once or multiple times, for example an S-shaped or wave-like profile, at least in sections. As a result of this bent profile, it is possible to obtain one or more defined bends of the light guide with one or more specific radii of curvature. Other profiles of the light guide that yield a defined bend are also conceivable. By way of example, in the case of an angled connector housing, for example configured as a 90° embodiment or 120° embodiment, the light guide can merely follow this bend, as a result of which it is already possible to obtain mode mixing. However, connectors or connector housings which tend to have a straight configuration have become established for the applications mentioned at the outset, and so the S-shaped light guide guidance, at least in sections, represents a preferred variant. Arrangements in which the light guide is guided in one or more loops are also conceivable.

It is particularly advantageous here if the region of the receiving section is embodied as a light guide receiving groove. Therein, the light guide can be guided in defined fashion in terms of its relative position and with the desired radii of curvature. The light guide receiving groove is embodied in at least one receiving shell, preferably in U-shaped fashion. In respect of the geometry or dimensions of the light guide receiving groove, it was found that the depth of the light guide receiving groove should correspond to at least 1.1 times, preferably at least 2 times the diameter of the light guide. What this can achieve during assembly is that the light guide can be held or a fixed, at least during assembly.

The fitting can be simplified if, directly at the light guide receiving groove and at least in sections, the wall of the light guide receiving groove merges, in particular without a step, into one or more fixation pins which, in the assembled state of the connector housing, engage in receptacles corresponding to the contour of the fixation pins in the respective other receiving shell. Here, the fixation pins additionally prevent the fibre from jumping out when it is laid into the light guide receiving groove. Moreover, this ensures sufficiently accurate positioning of the receiving shells during the assembly.

In respect of the fitting outlay, it is particularly cost-effective if the connector housing can be plugged together from the individual elements by means of latching connections.

In respect of simple handling in practice, it is particularly advantageous if the connector housing has an inner region, including the receiving section for the light guide, the receiving shells and/or the guide elements, and an external housing, wherein the inner region is configured to be freely rotatable, through an angle of rotation of more than 360°, in relation to the external housing. This avoids torsional stresses, which could damage the light guide, when fastening the light guide to the laser light source.

If the connector housing has at least one RFID chip for identifying and/or for storing characteristic physical properties of the emission element and if the laser light source has pertinent receiving or reader units corresponding therewith, as provided by a particularly preferred embodiment variant, data, for example certain characteristic variables relating to the emission characteristic of the emission element or relating to efficiency, can be stored and read and used during operation with the laser light source, for example during operation of a medical diagnostic or therapy device for exactly setting the power or calibrating the laser light source. Moreover, access codes could also be stored in encrypted fashion; these facilitate a unique identification and consequently identify possibly unsuitable or unapproved plagiarized products. This increases the safety for the patient and the user.

It is also conceivable to store or set a so-called flag on the RFID chip as soon as the component has been connected to the laser light source a single time. Should the component be plugged in a second time, reading of the flag allows recognition that the component has already been used and blocks the laser light source from use. This can prevent components actually provided for a single use from being used multiple times, which is useful for patient safety, in particular. Such RFID chips are available in simple embodiments with only a small memory capacity, for example for storing a characteristic, up to embodiments in which a plurality of kilobytes of information can be stored. In a preferred embodiment, the connector housing has a corresponding RFID chip receiving section for receiving such an RFID chip.

Embodiments, possibly with reduced functionality, which have other mechanisms for identifying and/or storing characteristics and/or safety data, for example encoding by means of colour, changeable staining, barcodes and/or QR codes, are also conceivable.

In a further advantageous embodiment variant, provision can be made for the connector housing to have a device by means of which the light guide, after a single use at the laser light source, is at least partly damaged or capped or displaced, for example in mechanical fashion, within the scope of removing the connector from the laser light source or within the scope of releasing the connection between laser light source and connector. Such apparatuses are known from U.S. Pat. No. 9,304,271 B2 of the applicant. Described therein is a connecting element for a single connection and single release of a fibre-optic light guide to or from a light source, comprising a housing with a wall which surrounds a cavity, a fibre-optic light guide passing through the housing and the cavity, a connecting piece corresponding to a connecting section of the light source for establishing the connection to the light source, with the connecting section being reusable post release, and means for preventing a repeated functional use of the connecting element and/or of the light guide. Within the scope of the first use of the connecting element, the fibre-optic light guide is connected by means of the connecting piece to the corresponding connecting section, which is situated in the housing of the light source, for example. Subsequently, the treatment, for example the PDT treatment, is carried out by virtue of the radiation generated by the light source being transmitted through the light guide to the site of the human body to be treated. Once the treatment is complete, the fibre-optic light guide and the connecting element are separated from the light source. The means ensure that the connecting element and/or the light guide can no longer be functionally used. Should the connecting means no longer be functional, it is no longer possible to establish a connection to the light source and/or ensure optimal light input coupling. The latter is expressed in terms of a significant decrease in the efficiency. By contrast, if the light guide is destroyed or at least partly damaged, it is no longer possible to transport radiation to the site of the human body to be treated. Although it is conceivable that the connection to the light source can be established in this case, modern light sources can have monitoring devices which immediately communicate to the treating physician that no radiation dose or an insufficient radiation dose has arrived at the distal end of the light guide and that a different, unused light guide must be used. Consequently, both cases ensure that a light guide that has already been used is not used a second time.

Here, the illumination system provides a light guide as a multimode quartz fibre, low-water quartz fibres for application wavelengths up to approximately 2.5 μm, in the case of very short application lengths up to nearly 3 μm, or particularly water-enriched quartz fibres for application wavelengths in the UV range, with round, substantially circular, hexagonal or any other polygonal-like or irregularly formed core cross-sectional structure. As a result of the above-described measures in the connector housing, it is possible, in particular, to use round quartz fibres, which are available particularly cheaply. Quartz fibres with a hexagonal or any other polygonal-like or irregularly formed core cross-sectional structure additionally help to reduce the sensitivity to NA variations of the laser light source described at the outset, but are more expensive in production, as has already been mentioned. As a matter of principle, it is also possible to use other fibre types, for example so-called HCS fibres, which have a quartz core and polymer cladding, or else IR fibres which can transmit IR light in the wavelength range >2 μm, in particular. Examples for this include, inter alia, so-called chalcogenide fibres, fluoride fibres or else hollow core fibres or PCF fibres. Glass optical fibres (GOF) made of, e.g., multicomponent glasses can be used in the visible wavelength range including an NIR range to approximately 1 μm, and also polymer optical fibres (POF), provided this is allowed by the amount of radiation to be guided to the diffuser.

In respect of the minimum permitted bend radius (minimum bend radius), the literature contains specifications or guidelines, to the effect that the minimum bend radius should not drop below 100-times to 200-times the diameter of the multimode quartz fibre in relation to its cladding diameter (core plus cladding, without buffer material) for a predominantly static long-term bending load, which would correspond to a minimum bend radius of 44 mm to 88 mm in the case of a quartz fibre with dimensions of 400/440 μm for the core/cladding diameter.

However, these specifications relate in part to a different considered service life and to different outage probabilities due to a break, and so there is no absolute fixed limit in this case. Moreover, the quartz fibre can be preselected in respect of its mechanical resilience in respect of bending loads by way of a so-called proof test, in which the quartz fibre is pulled over a linear arrangement of rollers following the drawing from the preform. This is also referred to as a proof test level. The latter is usually located in a range from 75 kpsi (corresponding to approximately 517 MPa) to 150 kpsi (corresponding to approximately 1034 MPa), depending on the roller diameter employed during this test. Therefore, the factor between minimum bend radius and cladding diameter can also be lower if the proof test level is set higher. Therefore, in a preferred embodiment variant, provision is made for a minimum bend radius of the light guide embodied as a multimode quartz fibre in the region of the receiving section to correspond to at least 60 times, preferably at least 100 times the diameter of the light guide in relation to its cladding diameter. A bend radius of approximately 40 mm of the quartz fibre in the region of the receiving section would in this case correspond to a factor of approximately 91 in relation to the aforementioned fibre geometry. In relation to a service life of 10 years, this bend could be maintained with a virtually 0% outage probability due to a break already by using a proof test level above 100 kpsi (corresponding to approximately 690 MPa).

Here, provision can be made in a further embodiment variant for the multimode quartz fibre used as a light guide to have at least one portion in the region of the receiving section at the end of the receiving section, downstream of the bend in the fibre in the direction of light propagation, in which portion the cladding of the quartz fibre is replaced by a coating material which has a higher refractive index than the refractive index of the core of the quartz fibre. This is advantageous if a high proportion of cladding modes, which are usually undesirable, are generated, for example as a result of the bend in the quartz fibre. The proposed measure allows these disturbing cladding modes to be output coupled.

In the process, this component of the laser light that is output coupled is absorbed in the region of the receiving section of the light guide. A better heat distribution can be obtained by additional metal parts in the connector housing, which serve as a heat sink and, in particular, are disposed in the receiving section, as a result of which instances of local overheating can be avoided. Advantageously, the illumination system has a heat sink in or on the connector housing, in particular in the receiving section.

It is particularly advantageous if the connector is embodied as a commercially available SMA connector, for example the SMA-905 type, or as an FC connector, and the connector housing has a corresponding connector receiving section for receiving the connector in a manner secured against rotation. This can ensure a defined relative position of the light guide in the connector housing and, in particular, in the receiving section for the light guide. Here, provision can be made for a union nut for affixing the connector in the laser light source to be fastenable in the external housing in a manner secured against rotation.

In view of increased robustness, it is particularly advantageous if the receiving section for the light guide has devices for protecting the fibre, i.e., protective elements, for example embodied as a protection against kinking and/or for strain relief. This can be obtained both by the relative position of the guide elements and by additional clamping sites in the connector housing. The use of heat-shrink tubing, which is pushed over the light guide at least in sections and affixed to the light guide by the receiving shells, is advantageous in this case.

In a particularly preferred embodiment, the connector housing and its individual components consist of plastic injection moulding parts, which can be realized in a particularly cost-effective manner. What is advantageous here is that even complex functionalities are able to be introduced relatively easily into the design. In view of the use in the medical sector it is furthermore advantageous if the employed plastic is preferably made from a biocompatible plastic material listed, for example, in the EN ISO 10993-1:2018 or EN ISO 10993-5:2009 or USP Class VI standards. Moreover, the material used should be selected in such a way that it is sterilizable, in particular ethylene oxide sterilizable (EO) since this sterilization process is of interest in the medical sector, particularly in the case of disposable applications or single use applications, as described in ISO 11135:2014. Here, care should be especially taken that the material has no chlorine since otherwise chlorine-containing compounds could arise during the EO process, which firstly could be toxic and secondly might only be driven out incompletely following the sterilization process.

In a particularly preferred embodiment, the illumination system has emission elements as a cylindrical diffuser with substantially radial emission characteristic, a spherical diffuser with a substantially spherical emission characteristic or a frontal diffuser with a substantially homogeneous emission characteristic in the distal direction. Use is also made of cylindrical diffusers with a radial emission, which can have a sectionally directed emission characteristic, for example over only 90° or 120° of the circumference as a result of partly applied layers, reflective layers and/or absorbent layers. Particularly in the case of the cylindrical diffusers, as mentioned the outset, it is possible to ensure defined emission characteristics independently of possible NA variations using the embodiment of the connector housing according to the invention, and this can be ensured over typical diffuser lengths of 40 to 50 mm. However, the homogeneity or the beam quality can also be improved using the aforementioned measures in the case of frontal diffusers, which by way of example have lens elements at the distal end thereof, for example so-called grin lenses (gradient index lenses).

What can be achieved in a preferred embodiment variant is that the emission behaviour of the emission element, embodied as a cylindrical diffuser, varies in the case of a range of variation ranging from at least 0.08 to 0.24, preferably also ranging from 0.05 to 0.30, of the numerical aperture $NA_L$ of the laser light source of the laser light from the laser light source coupled into the connector, in such a way that the emission intensity, measured as relative luminance, at the diffuser surface drops no more than 40%, particularly preferably by no more than 20%, over its length in relation to its maximum value of the relative luminance. In particular, this can minimize or completely solve the problems mentioned the outset.

A preferred use of the illumination system, as described above in its various embodiment variants, provides for the use in photodynamic therapy (PDT) or photoimmunotherapy (PIT) for tumour therapy, for example, in endovenous laser treatment (EVLT) for treating varicose veins, for example, in laser interstitial thermal therapy (LITT) or in applications in the fields of dentistry, ophthalmology or dermatology, as described at the outset. In the field of dentistry, applications for wound or periodontitis treatment, in particular, should be mentioned. Moreover, there are applications in brain research, in which individual brain regions can be stimulated by means of light and hence pathological symptoms can be treated therewith.

Moreover, industrial applications also conceivable, for example for inspecting hard to access locations, for example on or in a machine, where homogeneous illumination is particularly important, or else spectroscopic applications or applications in biochemistry, in which biochemical in vitro reactions are stimulated by light.

BRIEF DESCRIPTION OF THE DRAWINGS

The invention will be explained in more detail below on the basis of an exemplary embodiment illustrated in the figures. In detail.

DETAILED DESCRIPTION

Figure 1:
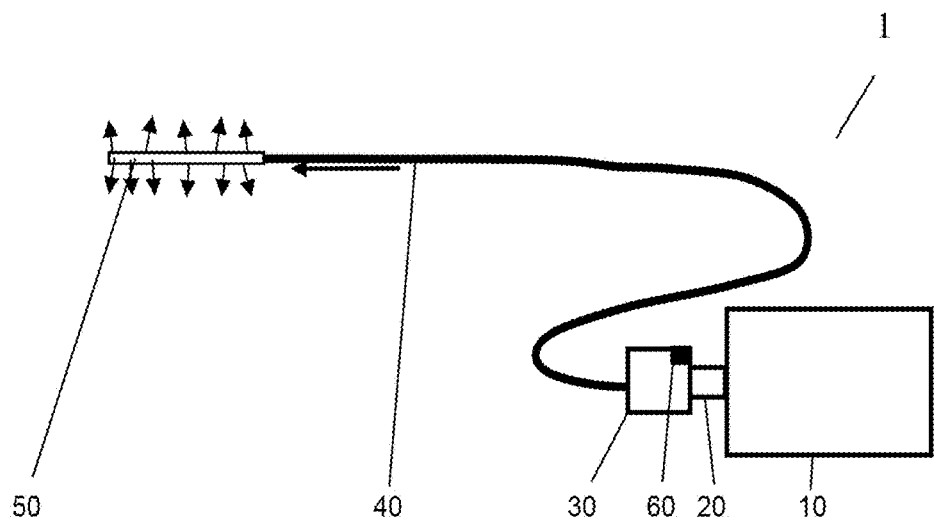
FIG. 1 schematically shows an illumination system with a light guide, an emission element and a connector with a housing for operation at a laser light source, FIG. 2 schematically shows the principle of the solution according to the invention.

FIG. 1 schematically shows the setup of an illumination system 1 according to the invention. A medical PDT application is illustrated in exemplary fashion in this case.

In the shown example, the illumination system 1 consists of a laser light source 10, which emits light in a certain spectral range when in operation. For PDT or PIT applications, as described the outset, use is made of lasers which emit at a wavelength matched to a biochemically modified dye (photosensitizer) administered previously, usually in the visible range, for example in the green spectral range at 532 nm or in the red spectral range at 690 nm, for example. A light guide 40 is connected at its proximal end to the laser light source 10 using a connector 20. At the distal end, the light guide 40 has an emission element 50 which is embodied as a cylindrical diffuser. As a rule, multimodal quartz fibres are used as light guides 40, wherein the connectors 20 are embodied, as a rule, as coaxial plug-in connectors, so-called SMA connectors or FC connectors, in which the fibres are adhesively bonded into the connector 20. Connectors 20 with nickel silver sleeves can also be advantageous in respect of the thermal resilience; here, the light guide 40 is introduced, for example crimped, into the nickel silver sleeve in interlocking fashion by way of a plastic deformation. Moreover, in the case of greater laser powers, use can also be made of connectors 20 in which the fibre end of the light guide 40 is protected by conical prism; this may be advantageous in the case of misalignments.

Moreover, the connector 20 comprises a connector housing 30 which simplifies handling. Here, these connector housings 30 can have a pertinent coloured configuration or have specific contours in order to facilitate a simple identification of and/or distinction between different types and/or fields of use or purposes of use. Moreover, additional information, such as the manufacturer name, designation, batch or serial number (LOT or S/N), could be printed thereon or engraved therein by means of a laser; these have in the meantime become mandatory for many medical products according to the UDI (unique device identifier) specifications, for example the corresponding FDA regulations. In this context, machine-readable 2-D pixel codes are increasingly also applied, for example as a so-called GS1 code, which may contain a multiplicity of individual items of information. To store this and further information, which may be important for the correct settings of the laser light source 10, for example, the housing 30 can also have a so-called RFID chip 60, which is able to communicate with pertinent reader units or receiver unit in the laser light source 10.

Figure 2:
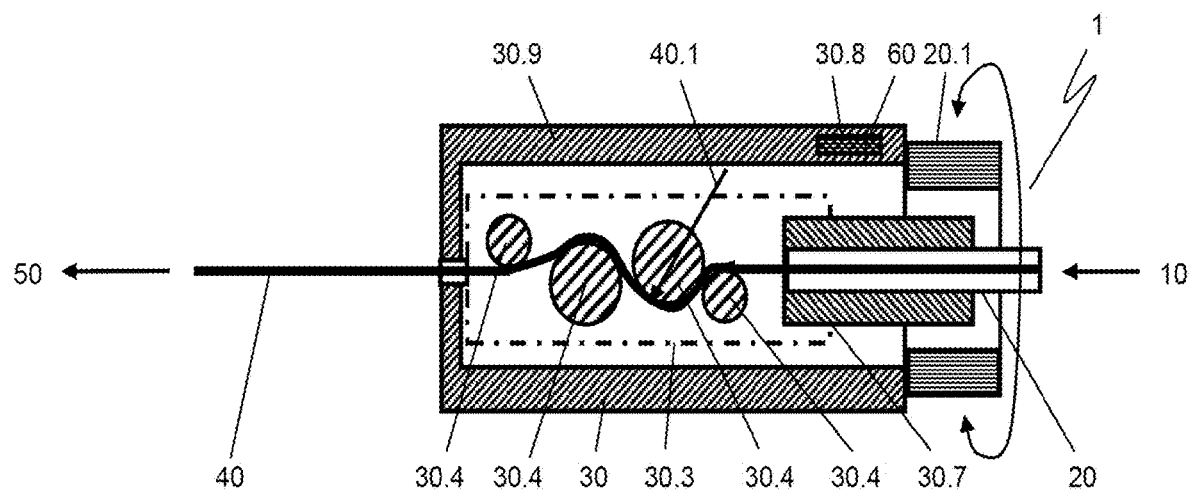

FIG. 2 shows the principle of the invention in a further schematic illustration. A connector housing 30 is illustrated; it has devices for stabilizing and narrowing a range of variation of a numerical aperture NA of the laser light coupled into the connector 20, which comes from the laser light source 10. According to the invention, the connector housing 30 has, in its interior, at least one guide element 30.4 in a receiving section 30.3 for the light guide 40, preferably a plurality of such guide elements for targeted bending of the light guide 40. The at least one guide element 30.4 can be embodied as a cylindrical and/or conical stud and/or as a sphere, around which the light guide 40 is guided in defined fashion, at least in the receiving section 30.3, as shown schematically by FIG. 2. Here, the quartz fibre used as a light guide 40 is fixated in a spatially defined fashion in terms of its relative position. Here, the exact geometry of the guide element or elements 30.4 is chosen in such a way that the bend radius 40.1 of the fibre in the region around these guide elements 30.4, resulting therefrom, is no less than 60-times the fibre diameter (in this case, the cladding diameter) in any case and is preferably at least 100-times the fibre diameter. Using the example of a quartz fibre with a round core diameter and typical dimensions in respect of its structure of 400/440/470/700 µm for core diameter/cladding diameter/hard clad diameter/buffer diameter, a minimum bend radius 40.1 of 26.4 mm or 44 mm arises. In the specific exemplary embodiment, the minimum bend radius 40.1 in the region of the receiving section 30.3 is 40 mm, which corresponds to a factor of approximately 91 between bend radius and fibre diameter, in relation to the diameter of the cladding.

This ensures that the quartz fibre is not mechanically overloaded and stable in the long term. As likewise shown schematically in FIG. 2, the connector housing 30 moreover has a connector receiving section 30.7 for receiving the connector 20 in a manner secured against rotation, which forms a solid unit with the receiving section 30.3 with the guide elements 30.4. The connector housing (30) furthermore has an external housing 30.9, in such a way that the latter is mounted in freely rotatable fashion (>360° angle of rotation) in relation to the inner region with the receiving region 30.3. Moreover, provision can be made for a union nut 20.1 for affixing the connector 20 in the laser light source 10 to be fastenable in the external housing 30.9 in a manner secured against rotation. Here, latching connections for securing the connector 20 in the laser light source 10 are also conceivable.

In a further configuration option, the connector housing 30 can have an RFID chip receiving region 30.8 for receiving the RFID chip 60. By way of example, this RFID chip 60 can be embodied as a circuit board ring.

Figure 3:
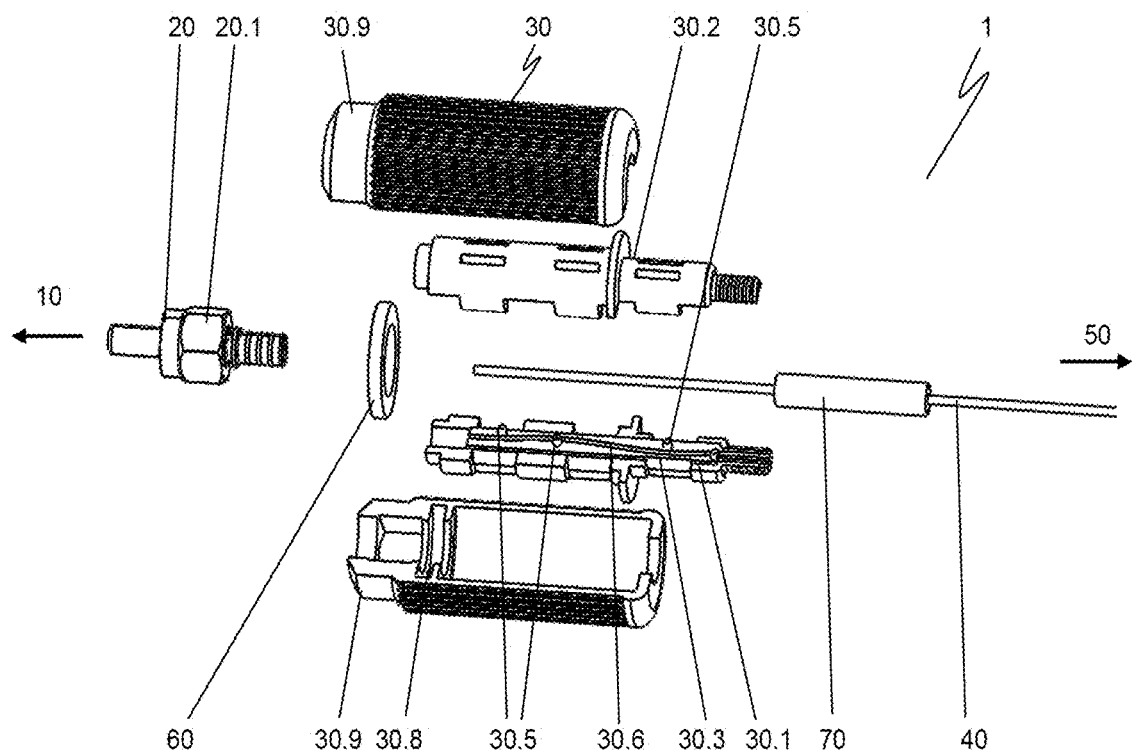
FIG. 3 shows an exploded view of a connector housing according to the invention, with the individual housing parts and further components.

FIG. 3 schematically shows a setup of the connector housing 30 with the individual housing parts as a specific embodiment of the invention in an exploded view.

Accordingly, the connector housing 30 has at least two receiving shells 30.1, 30.2, in which at least one of the receiving shells 30.1 of the housing 30 forms the receiving section 30.3 for receiving the light guide 40. In the shown example, the light guide 40 has an S-shaped profile, at least in sections, in the region of the receiving section 30.3. In the shown example, the region of the receiving section 30.3 is embodied as a light guide receiving groove 30.6, which preferably has a U-shaped embodiment. Here, provision is made, directly at the light guide receiving groove 30.6 and at least in sections, for the wall of the light guide receiving groove 30.6 to merge without a step into one or more fixation pins 30.5 which, in the assembled state of the connector housing 30, engage in receptacles corresponding to the contour of the fixation pins 30.5 in the respective other receiving shell 30.2.

In this case, the light guide 40 is guided in the receiving section 30.3, specifically in the light guide receiving groove 30.6 here, in such a way that the bend radius arising therewith does not exceed the admissible bend radius. For the shown example, a quartz fibre with the following geometries is used as a light guide 40:

| | |
|---|---|
| Core diameter | 400 μm |
| Cladding diameter | 440 μm |
| Plastic cladding (hard clad diameter) | 470 μm |
| External diameter with protective sleeve (buffer) | 700 μm |

According to the boundary conditions in respect of the minimum admissible bend radius, highlighted above, a bend radius of approximately 40 mm arises accordingly in the example shown.

The two receiving shells 30.1, 30.2 form an inner region in the connector housing 30, which inner region is mounted to be rotatable freely by more than an angle of rotation of 360° in relation to the external housing 30.9, which is likewise configured as two half shells in this case. Here, provision is made for the connector 20, an SMA-905 connector in the example shown, to be securely connected to the two receiving shells 30.1, 30.2. By contrast, the external housing 30.9 comprises a union nut 20.1 of the connector. What this can achieve is that, after the connector 20 has been inserted into the laser light source 10, the union nut 20.1 can be co-rotated by rotating the external housing 30.9 and hence the connector 20 can be affixed to the laser light source 10 in a secured fashion and in a defined fashion in respect of the distance.

In the example shown, the connector housing 30 has an RFID chip receiving section 30.8 in the two shells which form the external housing 30.9, an RFID chip 60 still being able to be placed therein prior to assembly. In the shown example, the latter is embodied as a ring-shaped circuit board. Furthermore, the strain relief or protection against kinking 70 is provided on the light guide 40; this can be embodied as tubing, preferably as heat-shrink tubing. It can additionally be clamped between the two receiving shells 30.1, 30.2 when the latter are assembled. In another embodiment variant, the heat-shrink tubing can also be shrunk onto the receiving shells 30.1, 30.2. Moreover, this strain relief or the protection against kinking 70 can additionally be printed, for example with information in respect of the component type, with a serial number and/or with a batch number.

Particularly preferably, the connector housing 30 with its individual elements described above is embodied to be able to be plugged together by means of latching connections.

Figure 4:
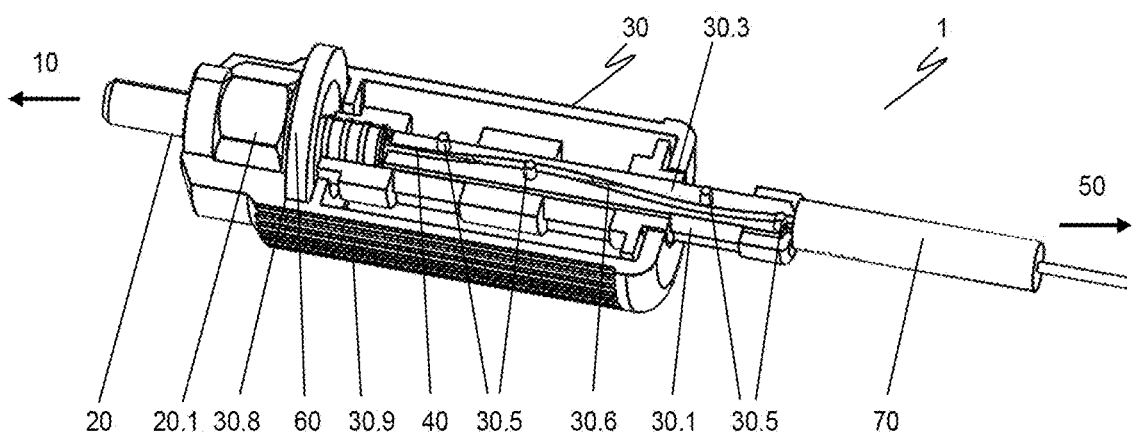
FIG. 4 shows a sectional view of the connector housing, FIGS. 5a and 5b each show a graph that highlights the influence in the scattering behaviour in the case of a cylindrical diffuser for NA variations, and FIGS. 6a and 6b each show further graphs of the effects of the measures according to the invention on the emission behaviour in the case of a cylindrical diffuser.

FIG. 4 shows, in a 3D view, a sectional view of the connector housing 30, as described in FIG. 3, in the assembled state.

FIG. 5a and FIG. 5b schematically show, in each case in a graph 100, different profiles of a spatially dependent scattering coefficient 101 as a function of the distance to the light input coupling 102. Here, the spatially dependent scattering coefficient 101 $k_{(x)}$ in $mm^{-1}$ represents an empirically determined material property relating to the amount of light that is diffusely scattered out of the diffuser in the lateral direction. In the case of a constant concentration of scattering elements along the longitudinal axis of the diffuser main body, the intensity curve typically has an exponential decrease with $I_{(x)} = I_0 \times e^{-x/k(x)}$. By way of a pertinent arrangement and number of scattering elements in the diffuser main body, the targeted profile for the spatially dependent scattering coefficients $k_{(x)}$ can be set in a targeted fashion in conjunction with the input coupling NA of a laser light source.

FIG. 5a shows a measured curve profile for instances of light coupling into the connector 20 with different numerical aperture NA. A profile region without mode mixing 103 shows the measured range of variation of the spatially dependent scattering coefficient, or the range of variation calculated therefrom, as a measure for the component of the light that is diffusely scattered out of the diffuser in the lateral direction and consequently also as a measure for the homogeneity thereof, for an NA of 0.08 to an NA of 0.24. Without the mixer, FIG. 5a shows a strong dependence on the input coupling NA at the connector 20. Between the two extreme values of NA=0.08 and NA=0.24, it is possible to determine a factor of almost 2 for the scattering coefficient, which, in respect of the design, corresponds to a factor of 2 for the number of scattering filaments to a first approximation (cf. DE 102017122756 A1 in this respect).

Only a minimal dependence can be determined in the case of a connector-side use of the mode mixer, as shown in FIG. 5b. Here, the family of curves with a mode mixer (profile region with mode mixing 104) lies at the level of the measurement without the mixer at maximum input coupling NA at the connector 20.

FIGS. 6a and 6b show the effects of the mode mixer on a measured profile for relative luminance 105 as a function of the distance to the light input coupling 100 in further graphs 100. Both figures show the typical profile using the example of a cylindrical diffuser with a 40 mm diffuser length. Here, the setup of the diffuser corresponds to the setup described in DE 102017122756 A1.

FIG. 6a very clearly shows the dependence on the input coupling NA. In the case of a diffuser design that is optimized for an input coupling NA of 0.08, it is possible to realize a good homogeneity with no more than a 30% drop in relation to maximum intensity (=100%) over the diffuser length. By way of example, if the input coupling NA is increased to a value of 0.24, the drop in the intensity profile is up to 55% in relation to the maximum value; as a rule, this is no longer suitable for PDT or PIT applications.

By contrast, FIG. 6b shows the NA dependence of the measured relative luminance 105 with a mode mixer as described in FIGS. 3 and 4. The profile in the case of an input coupling NA of 0.08 and in the case of 0.24 show very similar profiles. Naturally in this case, as described above, the curve in the case of the maximum NA (0.24 in this case) is also adopted in the case of input coupling NA of 0.08. However, this can be subsequently corrected in a targeted fashion when designing the diffuser by way of reducing the number of scattering elements in the diffuser main body, as is described in DE 102017122756 A1.

What this measure, coupled with a mode mixer according to the invention in the connector housing 30 as described above, can achieve is that, in the case of a cylindrical diffuser as an emission element 50, the emission intensity as a relative luminance 105 measured at the diffuser surface drops by no more than 40%, particularly preferably by no more than 20%, over its length in relation to the maximum value of the relative luminance 105 (=100%), wherein the numerical aperture $NA_L$ of the laser light source 10 and of the laser light from the laser light source 10 thus coupled into the light guide 40 in the connector 20 can vary in a range from 0.08 to 0.24. In a particularly preferred embodiment variant, the range of variation could also be larger, for example between 0.05 and 0.30.

| | LIST OF REFERENCE SIGNS: |
|---|---|
| 1 | Illumination system |
| 10 | Laser light source |
| 20 | Connector |
| 20.1 | Union nut |
| 30 | Connector housing |
| 30.1 | First receiving shell |
| 30.2 | Second receiving shell |
| 30.3 | Receiving section |
| 30.4 | Guide element |
| 30.5 | Fixation pin |
| 30.6 | Light guide receiving groove |
| 30.7 | Connector receiving section |
| 30.8 | RFID chip receiving section |
| 30.9 | External housing |
| 40 | Light guide |
| 40.1 | Bend radius |
| 50 | Emission element |
| 60 | RFID chip |
| 70 | Protective element |
| 100 | Graph |
| 101 | Spatially dependent scattering coefficient |
| 102 | Distance from light input coupling at the cylinder diffuser |
| 103 | Profile region without mode mixing |
| 104 | Profile region with mode mixing |
| 105 | Relative luminance |

What is claimed is:

1. An illumination system, comprising:
a laser light source with a numerical aperture;
a light guide having a proximal end and a distal end;
a connector having a connector housing, the connector connecting and/or assigning the laser light source at the proximal end; and
an emission element at the distal end,
wherein the connector housing has a device configured to reduce an influence of a range of variation of the numerical aperture so that an emission behaviour of the emission element is independent of a range of variation of the numerical aperture, and
wherein the connector housing has an inner region that includes a receiving section, wherein the inner region is freely rotatable through an angle of rotation of more than 360° in relation to the connector housing.

2. The illumination system of claim 1, wherein the connector housing has the receiving section with a guide element, the light guide being in the receiving section and being bent by the guide element.

3. The illumination system of claim 2, wherein the guide element is selected from a group consisting of a cylindrical stud, a conical stud, a sphere, and wherein the light guide, at least in the receiving section, is guided in a defined spatial fashion in respect of a relative position and is bent so that a minimum bend radius is maintained.

4. The illumination system of claim 2, wherein the light guide is a multimode quartz fibre with a cross section selected from a group consisting of a circle, a hexagon, a polygon, and combinations thereof.

5. The illumination system of claim 4, wherein the multimode quartz fibre has a minimum bend radius in a region of the receiving section that is at least 60 times a cladding diameter of the light guide.

6. The illumination system of claim 2, wherein the receiving section further comprises a strain relief and/or a kink relief.

7. The illumination system of claim 1, wherein the connector housing is secured together by a latching connection.

8. The illumination system of claim 1, wherein the connector housing further comprises a heat sink.

9. The illumination system of claim 1, wherein the connector is an SMA connector or an FC connector, wherein the connector housing has a corresponding connector receiving section configured to receive the SMA connector or the FC connector in a manner secured against rotation.

10. The illumination system of claim 9, further comprising a union nut that affixes the connector in the laser light source, the union nut being in the connector housing in a manner that prevents rotation.

11. An illumination system, comprising:
a laser light source with a numerical aperture;
a light guide having a proximal end and a distal end;
a connector having a connector housing, the connector connecting and/or assigning the laser light source at the proximal end; and
an emission element at the distal end,
wherein the connector housing has a device configured to reduce an influence of a range of variation of the numerical aperture so that an emission behaviour of the emission element is independent of a range of variation of the numerical aperture,
wherein the connector housing has a receiving section with a guide element, the light guide being in the receiving section and being bent by the guide element, and
wherein the connector housing comprises two receiving shells disposed in an inner region, wherein one of the two receiving shells has the receiving section, and wherein the light guide, in a region of the receiving section, has an S-shaped or wave-like profile at least in sections.

12. The illumination system of claim 11, wherein the region of the receiving section is a light guide receiving groove.

13. The illumination system of claim 12, wherein the light guide receiving groove has a depth of at least 1.1 times an overall diameter of the light guide.

14. The illumination system of claim 12, wherein the light guide receiving groove has a wall that merges without a step into one or more fixation pins that engage in receptacles in a second of the two receiving shells.

15. The illumination system of claim 11, wherein the connector is biocompatible and sterilizable.

16. An illumination system, comprising:
a laser light source with a numerical aperture;
a light guide having a proximal end and a distal end;
a connector having a connector housing, the connector connecting and/or assigning the laser light source at the proximal end; and
an emission element at the distal end,
wherein the connector housing has a device configured to reduce an influence of a range of variation of the numerical aperture so that an emission behaviour of the emission element is independent of a range of variation of the numerical aperture, and
wherein the connector housing comprises an RFID chip that identifies and/or stores characteristic physical properties of the emission element, and wherein the laser light source comprises a receiving or reader unit that reads the RFID chip.

17. An illumination system, comprising:
a laser light source with a numerical aperture;
a light guide having a proximal end and a distal end;

a connector having a connector housing, the connector connecting and/or assigning the laser light source at the proximal end; and an emission element at the distal end, wherein the connector housing has a device configured to reduce an influence of a range of variation of the numerical aperture so that an emission behaviour of the emission element is independent of a range of variation of the numerical aperture, and wherein the connector housing comprises another device, upon removal or releasing the laser light source from the connector, is damaged or clipped or displaced.

18. An illumination system, comprising:

a laser light source with a numerical aperture;

a light guide having a proximal end and a distal end;

a connector having a connector housing, the connector connecting and/or assigning the laser light source at the proximal end; and an emission element at the distal end, wherein the connector housing has a device configured to reduce an influence of a range of variation of the numerical aperture so that an emission behaviour of the emission element is independent of a range of variation of the numerical aperture, wherein the connector housing has a receiving section with a guide element, the light guide being in the receiving section and being bent by the guide element, wherein the light guide is a multimode quartz fibre with a cross section selected from a group consisting of a circle, a hexagon, a polygon, and combinations thereof, and wherein the multimode quartz fibre has a portion in the region of the receiving section, downstream along a direction of light propagation of a bend in the multimode quartz fibre, wherein the portion has cladding replaced by a coating material, the coating material having a higher refractive index than a refractive index of a core of the multimode quartz fibre.

19. An illumination system, comprising:

a laser light source with a numerical aperture;

a light guide having a proximal end and a distal end;

a connector having a connector housing, the connector connecting and/or assigning the laser light source at the proximal end; and an emission element at the distal end, wherein the connector housing has a device configured to reduce an influence of a range of variation of the numerical aperture so that an emission behaviour of the emission element is independent of a range of variation of the numerical aperture, and wherein the emission element is selected from a group consisting of a cylindrical diffuser with a radial emission characteristic, a cylindrical diffuser with a directed emission characteristic, a spherical diffuser with a spherical emission characteristic, and a frontal diffuser with a homogeneous emission characteristic in the distal direction.

* * * * *